United States Patent [19]

Stuart

[11] Patent Number: 5,643,745
[45] Date of Patent: Jul. 1, 1997

[54] HETEROLOGOUS DIMERIC PROTEINS PRODUCED IN HETEROKARYONS

[75] Inventor: W. Dorsey Stuart, Kaneohe, Hi.

[73] Assignee: University of Hawaii, Honolulu, Hi.

[21] Appl. No.: 191,337

[22] Filed: Feb. 3, 1994

[51] Int. Cl.[6] .................... C12P 21/04; C12N 1/15
[52] U.S. Cl. ............. 435/69.1; 435/254.3; 435/69.4
[58] Field of Search ................... 435/69.1, 254.3, 435/69.4, 172.3, 254.11

[56] References Cited

U.S. PATENT DOCUMENTS

| | | | |
|---|---|---|---|
| 4,486,533 | 12/1984 | Lambowitz | 435/172.3 |
| 4,816,405 | 3/1989 | Yelton et al. | 435/243 |
| 4,880,734 | 11/1989 | Burke et al. | 435/69.1 |
| 4,885,249 | 12/1989 | Buxton et al. | 435/172.3 |
| 4,935,349 | 6/1990 | McKnight et al. | 435/69.5 |
| 5,177,193 | 1/1993 | Boime et al. | 530/397 |
| 5,364,770 | 11/1994 | Berka et al. | 435/69.1 |

FOREIGN PATENT DOCUMENTS 552569  7/1993  European Pat. Off. .......... C12N 5/12

OTHER PUBLICATIONS

Stuart, W.D. et al., "Cloning of *mtr*, an amino acid transport gene of *Neurospora crassa*", *Genome* (1988) 30:198–203.
Koo et al. "Sequence and structure of *mtr*, an amino acid transport gene of *Neurospora crassa*", *Genome* (1991) 34:644–651.
Dales et al., *J. Gen. Microbiol*, vol. 129, 1983, pp. 3637–3642.
Payton et al., *J. Bact.*, vol. 129, 1977, pp. 1222–1226.
Downey et al., *Mol. Cell. Biochem.*, vol. 59, 1984, pp. 155–163.

*Primary Examiner*—Mindy Fleisher
*Assistant Examiner*—James Ketter
*Attorney, Agent, or Firm*—Morrison & Foerster LLP

[57] ABSTRACT

The invention relates to a heterokaryotic filamentous fungus host capable of producing a heterologous heterodimer comprising at least two subunits. The heterokaryon contains a first and second nucleus; each nucleus contains an expression system for one subunit of the heterodimer. The heterokaryon is prepared by culturing together a first fungus host strain and a second fungus host strain that is homozygous with the first fungus host strain with respect to all heterokaryon compatibility alleles, wherein the first and second fungus host strains are cultured together under conditions wherein neither the first nor the second fungus strain can survive unless the heterokaryotic host is formed.

15 Claims, 4 Drawing Sheets

```
DNA Strider 1.0 ### Tuesday, June 15, 1993  10:07:28 AM

New 2.9 kb DNA seqn -> List

DNA sequence  2783 b.p.    AGATCCGCCTCG ... GATGTTCCAGGC   linear 10         20         30         40         50         60
      1  AGATCCGCCT CGCCCCAAGC GCATCCCAAC GCGGCGTGCT TATATGTCGC TCTTCCCTCT    60
     61  CACGTACCTC GCAAGTACCT GTCTCATCTG GCACCCGCCT TCTCCATCCC TCTTCTTCAC   120
    121  TACTTAATCT GCCCCGGTCC CCGCAGTTC ATCCTGTCTC TCAGACCTTG GATGTCTGT    180
    181  TGGTCTTTTC GCTTATTGTC GCTACCCCA TCCATATTA GCTTGAGAAG GGAAAATCAA    240
    241  CAGCATTTTC TCTTTCCCTC CGTACCCCA CATCCAAACA GCTTGAGAAG GGAAAATCAA    300
    301  GCCACTGTCG ACAAAGGCCT CTCTTTAGC CATCCAAACA CCCAACATGG ACTCGCAATA    360
    361  CGAGACAAAA AAGAATGACC TCAACAAGGC CTCTTTACCA CCAGAGTCAA ACGATGAGCA    420
    421  TGTTGGCGAG GTCCGGGGCT CAAACGCCAT CATGCCGTAC AAGGAGCCTG AGGCCCAGGA    480
    481  GGGCCATGCC AAGTTCCACC TGGGGGCCC CATGCATGCC AGGGTCGTCC TCATCGTGCC    540
    541  GGCCATTGCC CTCGGCTCTC GTCTCGGCTT GAAAATCGC ACCTACCCTTG GCATTATCGG    600
    601  TGGTGTTATT CTCTCTGTCG GCATGGGACT CCACTATGCC TACGGCTC ACGTTGGTCT    660
    661  ACAAACCAAG CTCAAGCACC CTGAAATCGC CATCAGCTT CTGCAACTGA TCTTCATCGT    720
    721  TGGAAGATGG GGATATGAAA TCATCAGCTT CATGTTTGTT CTGCAACTGA TCTTCATCGT    780
    781  CGGCTCCCAC GTCCTCACTG GCACCATCAT GTGGGGCACC ATCACGGATA ACGGCAACGG    840
    841  TACCTGCTCT CTCGTCTTCG GCATTGTCTC CGCATCATT CTCTTCCTCC TTGCCATTCC    900
    901  TCCCAGTTTC GCCGAGGTTG CCGAGGTTG ATACATCGAT TCGTCTCCCA CACCAGGAGG    960
    961  CATCCTCATC ACCATGATTG CTACTGGCAT TCGCTCGAGC CACCAGGAGG GTGGTCTCGC  1020
   1021  TGCTGTTCCC TGGTCTTGCT GGCCCAAGGA GGACCCTTAGC CTTGCTGACG GCTTCATTGC  1080
```

New 2.9 kb DNA seqn [347 to 1699] → 1-phase Translation

DNA sequence  2783 b.p.  AGATCCGCCTCG ... GATGTTCCAGGC  linear

```
347
ATG GAC TCG CAA TAC GAG ACA AAA AAG AAT GAC CCA ATC ATG CCG TAC CCA GAG
met asp ser gln tyr glu thr lys lys asn asp pro ile met pro tyr pro glu
407                                          11                  377
TCA AAC GAT GAG CAT GTT GGC GAG GTC CGC AAG AAC GCC ATG GAC ATG AAG GAG
ser asn asp glu his val gly glu val arg lys asn ala met asp met lys glu
467                                          31                  437
CCT GAG GCC CAG GGC CAT GCC AAG TTC CTC CGT GGC TGG AAA CGT CTG ACG GTC
pro glu ala gln gly his ala lys phe leu arg gly trp lys arg leu thr val
527                                          51                  497
GTC CTC ATC GAG GAG GCC ATT GCC CTC GGC TCT CCC GGC GCC TTC GCT ACC
val leu ile glu glu ala ile ala leu gly ser leu pro gly ala phe ala thr
587                                          71                  557
CTT GGC ATG GTG CCT GGT CAA CTC ATT CTC TCT GGC ATG CTC ATC TAC ACG
leu gly met val pro gly gln leu ile leu ser gly met gly leu ile tyr thr
647                                          91                  617
GCT CAC GTT ATC GGA CAA ACC AAG CTC TCT GTC CAC CCT GAA CTC ATC TAC ACG
ala his val ile gly gln thr lys leu ser val his pro glu leu ile tyr thr
707                                         111                  677
GGT CGT TTT GGA AGA TGG GGA TAT GAA ATC ATC GGC ACC ATT GTT CTG CAA
gly arg phe gly arg trp gly tyr glu ile ile gly thr phe val leu gln
767                                         131                  737
CTG ATC TTC GTC GGC CAC TCC GTC CTC GTC ACT ATG TTC TCC GGC ATC ATC ACG
leu ile phe val gly his ser val leu val thr met phe ser gly ile ile thr
827                                         151                  797
GAT AAC GGC ACC GGT GCC ATT CCC AGT TTC GCC GAG GTT GGA TAC TGG GCC TTC
asp asn gly thr gly ala ile pro ser phe ala glu val gly tyr trp ala phe
887                                         171                  857
CTC CTT GCC ATT CCT CCC ATC CTC GTT GCT GCC ATT ACC ATG TTT GGA CAC CAG
leu leu ala ile pro pro ile leu val ala ala ile thr met phe gly his gln
947                                         191                  917
TCC ATC TGC AGT TTT GCC ATC CTC GTC TGC AGT CGG ACT GAT TTC GTC
ser ile cys phe gly ile arg ser leu val cys ser arg ser asp phe val
1007                                        211                  977
GAG GGT GGT CCA GGT GCT GTT GCC CCC AAG GAG GAC TTC GCC ATG CAC CAG
glu gly gly pro gly ala val ala pro lys glu asp phe ala met his gln
1067                                        231                 1037
GAG GGC ATT GCT GTC AGC AAC ATC GTT TGC TGG AGC CTT GCT
glu gly ile ala val ser asn ile val cys trp ser leu ala
                                            251                 1097
```

FIG.2B

```
1127/      261
AGC TTT ATG GAT GAG ATG CAC ACC CCC TCC AAG TCC ATC GTT GCT CTC CGC
ser phe met asp glu met his thr pro ser lys ser ile val ala leu gly
1187/      281
TTG ATT GAA ATC TTC TAC ACC TAC GTT ACT GTT GCT TAC GCT TTC GGC CCC
leu ile glu ile phe tyr thr tyr val thr val ala tyr ala phe gly pro
1247/      301
GAG GTC CAG TCT CCT GCC TTG CTC CTC TCT AAG CTC GTC GCT AGC TTC GGT
glu val gln ser pro ala leu leu leu ser lys leu val ala ser phe gly
1307/      321
ATT GCC CTC ATC TTC ATC TTC CCA GGC TCT CGT GGC AGC GCG GGT AGG TAT
ile ala leu ile phe ile phe pro gly ser arg gly ser ala gly arg tyr
1367/      341
CTG GAG CGC ATC TGG CCC AAC GTC GTA ATT GCT CTC ACC GCT GAC GCC TGG
leu glu arg ile trp pro asn val val ile ala leu thr ala asp ala trp
1427/      361
ATG GTT TGG CTT GGT TTT GAC CTG TAT CGT GTT ATT TCC GGT TTT AGC
met val trp leu gly phe asp leu tyr arg val ile ser gly phe ser
1487/      381
ATC CCT TTC TTC GAT CTG CTG TGC TCG CTC ACC AAG AGC AGC CAG ATT CTT
ile pro phe phe asp leu leu cys ser leu thr lys ser ser gln ile leu
1547/      401
TTC TAT CCT GCC ATG TAT TTC ATC ACC AGG ATG GGC GGT ATT CTT GTT TAC
phe tyr pro ala met tyr phe ile thr arg met gly gly ile leu val tyr
1607/      421
AAG AAG TAC TTG GAT GCC CTC AAC ATG CTC TGC TTC CAG CTC TCT GTT TAC
lys lys tyr leu asp ala leu asn met leu cys phe gln leu ser val tyr
1667/      441
GGT ATT ACC TAC GCC ATT CAG GAC ATT GTA AGT TTG GCC CGC TTT TCT GTT TAC
gly ile thr tyr ala ile gln asp ile
1727/                                  1759/
TCT TTG CAC ACA AAT GCT AAC TTG CTT CTC AG ATG GAC CGT TAC GAC CAT GGC AAG GTT
                                           met asp arg tyr asp his gly lys val
1789/
TCC AAG CCT TAT AGC TGT GCG CCC TTG GCT TAA
ser lys pro tyr ser cys ala pro leu ala OCH
```

HETEROLOGOUS DIMERIC PROTEINS PRODUCED IN HETEROKARYONS

FIELD OF THE INVENTION

The present invention relates generally to the expression of heterologous genes in filamentous fungi, more specifically to the expression of genes encoding heterodimeric proteins by heterokaryotic filamentous fungi host cells.

DESCRIPTION OF THE RELATED ART

The cloning and expression of heterologous genes in bacteria, yeast and fungi have been recognized as a viable means for producing a variety of useful proteins. Expression of heterologous genes in these microorganisms has generally relied on the use of autonomously replicating extrachromosomal elements, widely known as plasmids. For example, Lambowitz, U.S. Pat. No. 4,486,533 issued Dec. 4, 1984, discloses the autonomous replication of DNA vectors for filamentous fungi by mitochondrial plasmid DNA. The mitochondrial plasmid DNA may be joined to another replicating system to provide a shuttle vector to enhance the convenience of genetic manipulation. Yelton et al., U.S. Pat. No. 4,816,405 issued Mar. 28, 1989, describes tools and systems that enable the modification of important strains of filamentous ascomycetes to produce and secrete large quantities of desired heterologous proteins Buxton et al., U.S. Pat. No. 4,885,249 issued Dec. 5, 1989, discloses the transformation of *Aspergillus niger* by a DNA vector that contains a selectable marker capable of being incorporated into the host *A. niger* cells. The vector may also contain other foreign DNA sequences required to enhance or modify the expression of proteins. McKnight et al., U.S. Pat. No. 4,935,349 issued Jun. 19, 1990, discloses a method for expressing higher eukaryotic genes in Aspergillus involving promoters capable of directing the expression of a heterologous gene in Aspergillus and other filamentous fungi. Similar techniques have been used to clone the mtr gene involved with amino acid transport in *Neurospora crassa* ("*N. crassa*") and to verify the tight linking of the cloned DNA to genomic markers flanking this gene in vivo. Stuart, W. D. et al., *Genome* (1988) 30:198–203; Koo, K. and Stuart, W. D. *Genome* (1991) 34:644–651.

However, production of a heterologous, dimeric protein, which has two or more non-identical subunits, in a fungal host cell has required the transformation of a single host cell in one of the following two ways:

(1) by a single large, unwieldy vector carrying the sequences for both subunits; or (2) by two smaller separate vectors, each of which carries a DNA sequence encoding one of the subunits, on the assumption that at least some portion of the transformed cells will be capable of carrying both subunits sufficiently close together, spatially and functionally, to enable the simultaneous expression of both genes.

Burke et al., U.S. Pat. No. 4,880,734 issued Nov. 14, 1989, discloses DNA constructs having a transcription control region comprising two regions, a first transcriptional regulatory region and a second transcriptional initiation region, where the two regions may be derived from different sources. This two-part transcriptional control region was joined to a gene not naturally associated with the transcriptional control region. A terminator region was also present to provide an expression construct that can be introduced into a yeast host as a extrachromosomal element. The use of regulatory sequences for controlling transcription of a structural gene provided the ability to grow the host cells to a high density with little or no expression of the structural gene, and then to induce expression by changing the environmental conditions, e.g., metabolites, temperature, etc.

European Patent No. 552,569 published Jul. 28, 1993 discloses a method of fusing (a) an animal cell capable of proliferating in a basal medium and (b) an animal cell having the ability to produce a useful substance and the ability to proliferate in a complete medium, but not in the basal medium. The resulting fused cell has both the ability to produce the useful substance and to proliferate in the basal medium. (EP 552,569, column 1, lines 45–53.)

There remains in the art a need to produce a heterologous heterodimer in a reliable and efficient manner. None of the above disclosures provides a method to do so.

DISCLOSURE OF THE INVENTION

The invention is directed to a heterokaryotic filamentous fungus capable of producing a heterologous heterodimer comprising at least two non-identical subunits. The heterokaryotic fungus is the result of fusion of two complementary fungal strains. The fusion results because each of the parent strains supplies a requirement of the other under the conditions of culturing.

Thus, in one aspect, the invention is directed a method to prepare a heterokaryotic filamentous fungus containing a first nucleus which has been modified to contain an expression system for a first nucleotide sequence encoding one subunit of a heterologous heterodimer as well as a second nucleus modified to contain an expression system for the production of the other subunit of the heterodimer. The process involves fusing separate strains of the fungus, one containing the first nucleus and the other the second. The fusion results because the first nucleus also confers a first characteristic negatively affecting growth under specified conditions that is correctable by a first property conferred by the second nucleus, and conversely the second nucleus also confers a second characteristic negatively affecting growth under specified conditions that is correctable by a second property conferred by the first nucleus. Thus, the property conferred by each nucleus complements the characteristic confined by the other when the conditions are such that both properties are required for growth. In a simple example, each nucleus may contain a mutant genome which results in an inability to grow in the absence of a different nutrient. Fungi containing both nuclei, but not those containing only one, will be able to grow in the absence of both nutrients.

This aspect of the invention is thus a method to prepare the heterokaryotic fungus of the invention by culturing together the above first and second fungus strains under conditions that, due to the presence of the first and second characteristics of the nuclei, neither the first fungus nor the second fungus host strain can survive unless the heterokaryotic fungus is formed. The resulting heterokaryotic filamentous fungus can then be kept in a heterokaryotic state by maintaining the fused fungus in a culture medium under these same conditions.

When cultured under these same conditions to maintain the heterokaryotic state, the desired heterodimer protein can be recovered when the conditions also include those favorable for the expression of the nucleotide sequences encoding the subunits therefor. Thus, another aspect of the invention is production of the heterologous dimer by culturing the heterokaryotic fungus under these conditions and recovering the heterodimer.

In still other aspects, the invention is directed to a filamentous fungus heterokaryon comprising at least two nuclei, one of which contains an expression system for production of one subunit of a heterologous heterodimer and the other which contains an expression system for production of the other subunit of the heterodimer.

BRIEF DESCRIPTION OF THE DRAWINGS

FIG. 1 (SEQ ID NO: 1) shows the nucleotide sequence of an approximately 2.9 kb fragment of the N. crassa mtr gene containing the entire open reading frame as well as the promoter and transcription terminating signals.

FIG. 2 (SEQ ID NO: 2, SEQ ID NO: 3 and SEQ ID NO: 4) shows nucleotide and deduced amino acid sequences of the open reading frame of the mtr locus.

MODES OF CARRYING OUT INVENTION

In the present invention, advantage is taken of the ability of filamentous fungi to form heterokaryons; the heterokaryons can then be used to produce heterologous heterodimers.
Nature of Filamentous Fungi and Background Requirements for Heterokaryon Formation Fungi can occur in single mononucleated cells that yield filamentous multinuclear strands, yeast cells, fruiting bodies with diverse spores, and/or cells that are differentiated sexually. They can also exist in multinucleated forms. The principal element of the growing form of a fungus as a mold is the hypha, a branching tubular structure, about 2 μm–10 μm in diameter. Hyphae grow by elongation at their tips (apical growth) and by producing side branches. Thus, as a colony grows, its hyphae form a mass of intertwining strands.

Some hyphae penetrate into the culture medium on which the fungus is growing to absorb nutrients, while those hyphae that project above the surface of the medium constitute an "aerial mycelium." Most colonies grow at the surface of liquid or solid media as irregular, dry, filamentous mats. In most species, the hyphae are divided by cross-walls called "septa." These septa, however, have fine, central pores. Thus, even septate hyphae have nuclei that are embedded in a continuous mass of cytoplasm and, in effect, contain a multiplicity of nuclei in a transportable cytoplasm.

The term "filamentous fungi" refers to those fungi that can form a mycelium through a mass of branching, interlocking filaments and, although interrupted by cross walls, permit the passage of cytoplasm between compartments due to perforations in the cross walls. Many of these fungi form meiotic spores within a sac when propagated sexually. With the appropriate stimulation, however, the mechanism of which is not entirely understood, reproduction can occur asexually. In this manner of reproduction, spores known as "conidia" are borne externally at the tips of budding projections formed at various locations along the filaments.

The filamentous fungi of the invention are generally Phycomycetes, Ascomycetes, Basidiomycetes, and Deuteromycetes. The Phycomycetes include all non-septate, as well as some septate, filamentous fungi. Their asexual spores are of various kinds and include sporangiospores contained within sacs formed at the end of specialized stalks. Different species have different sexual cycles.

Ascomycetes are distinguished from other fungi by the ascus, a saclike structure containing sexual spores, known as ascospores. The ascospores are the end product of mating, the fusion of male and female nuclei, two meiotic divisions, and usually one final mitotic division. Basidiomycetes are distinguished by sexual spores that form on the surface of a specialized structure. The Deuteromycetes are often referred to as "imperfect fungi" because no sexual phase has yet been observed. Their hyphae are septate, and conidial forms are similar to those of the Ascomycetes.

The preferred heterokaryotic filamentous fungus is of the group Ascomycetes, more preferably, from the genera Neurospora, Aspergillus and Penicillium. Particularly useful species from Neurospora include N. intermedia, N. crassa, N. sitopula, and N. tetraspora.

Useful species of Aspergillus include A. nidulans, A. niger, A. terreus, and A. fumegatus.

A particularly preferred genus is Neurospora, of which the most preferred species is N. crassa.

The vegetative growth of filamentous fungi involves nuclear division with cell division (mitosis). This type of cell division consists of asexual reproduction, i.e., the formation of a new clone without the involvement of gametes and without nuclear fusion by way of conidia. For example, the species of Neurospora contain in their nuclei seven different chromosomes, each having a single copy, i.e., the vegetative organism is haploid. This haploid state is typically maintained during mycelial growth and during asexual reproduction through the formation of conidia.

Sexual reproduction can also occur, and then two haploid cells (hyphae or conidia) of different mating type fuse to form a dikaryotic cell containing two distinct nuclei. The two haploid nuclei thus coexist in the same cytoplasm and, for a time, divide more or less in synchrony. If a cell initiates ascospore formation, however, the two different haploid nuclei can actually fuse to form a diploid nucleus, which contains pairs of homologous chromosomes. This diploid cell then begins meiosis.

A "heterokaryon" is a cell with two (or more) genetically different nuclei. The heterokaryons of the invention must contain nuclei from cells that are homozygous for all heterokaryon compatibility alleles (except for the mating type allele when the tol gene is present). At least ten chromosomal loci have been identified for heterokaryon incompatibility: het-c, het-d, het-e, het-i, het-5, het-6, het-7, het-8, het-9 and het-10, and more are inferred to exist. Perkins et al., "Chromosomal Loci of Neurospora crassa", Microbiological Reviews (1982) 46:426–570, at 478.

If two strains carry different alleles at one or more het loci, they are unable to form stable heterokaryons. Protoplasmic killing occurs after fusion of unlike hyphae or after microinjection of cytoplasm or extracts into unlike strains. When duplications (partial diploids) are heterozygous for het one or more alleles, growth is inhibited and highly abnormal. A number of heterokaryon incompatibility loci (specifically, het-c, -d, -e, and -i) were first defined by heterokaryon tests. Het-5 through -10 loci were detected by using duplications, as differences at bet loci are common in natural populations. Id.

Mating type alleles "A" and "a" also act as het genes in N. crassa, although some slow heterokaryotic growth may occur. Microinjection experiments have implicated proteins in the killing reaction. Thus, opposite mating types are also generally important for the complex events associated with the proliferation of heterokaryotic ascogenous hyphae. Id. at 436 and 478. However, if the tol gene is present, the vegetative (heterokaryon) incompatibility associated with opposite mating type alleles A and a is suppressed without sexual compatibility being affected. Thus, (tol; A+a; a) heterokaryons can be fully compatible and stable if the other het loci are homokaryotic and A/a duplications grow normally when the tol gene is present.

If hyphae from two different strains that are homozygous for the compatibility loci are provided, they may fuse when grown in the same medium, in particular when fusion is forced as described below. The resulting culture will then contain nuclei from both strains circulating in the shared cytoplasm of a common mycelial mat.

Nature of the Parent Strains

Since each of the parent fungi used in the fusion will provide an expression system for a subunit of a heterodimer, one parent will have a nucleus modified to contain an expression system for a nucleotide sequence encoding a first subunit of a desired heterologous heterodimer and second fungus parent will have a nucleus modified to contain an expression system for a nucleotide sequence encoding the second subunit of the desired heterologous heterodimer, which is different from the first subunit. Transformation of each parent strain with DNA comprising an expression system for the relevant subunit is conducted using standard recombinant techniques, as further described below.

In addition to having been modified to contain the desired expression systems, the nuclei of each of the parent strains must contain a genome that results in a characteristic that renders the fungus dependent on the presence of the second nucleus for survival under the conditions provided for fusion to form the heterokaryon. Thus, the nucleus of each parent confers a characteristic which would result in the failure of the fungus in which it is contained to survive under the culture conditions unless the second nucleus is also present. For example, a parent that requires a particular nutrient may be cultured on a medium lacking the nutrient along with a parent that does not have this requirement. If hyphal fusion occurs, the nucleus of the second parent confers ability to survive in the absence of this nutrient. The second parent, in turn, may require a different nutrient, not required by the first. Only fungi containing both nuclei can then survive when both nutrients are lacking.

The required nutrient can be any substance which the fungus strain cell needs for growth or which, when absent, seriously impairs the ability of the fungus strain to grow or survive. Examples of useful nutrient requirements and the relevant mutants include:

(1) amino acids such as histidine (his-1 through -7 mutants), proline (aga mutants), arginine (arg-11 mutants), citrulline (arg-11 mutants), asparagine (asn mutants), choline (chol-1 and chol-2 mutants), cysteine (cys-1 mutants), glutamine (gln-1 mutants), leucine (leu-1through -4), lysine (lys-2, -4 and -5), methionine (mac mutants and met-6, -9 and -10 mutants), and threonine (thr-2 and -3 mutants);

(2) mixtures of aromatic amino acids, such as a mixture of p-aminobenzoic acid, tyrosine, tryptophan, and phenylalanine (required by all aro strains except aro-6, aro-7 and aro-8), a mixture of tryptophan and phenylalanine (required for aro-6 mutants), a mixture of isoleucine and valine (required for ilv-1, -2 and -3), and a mixture of phenylalanine and tyrosine (required for pt mutants);

(3) vitamins such as pantothenic acid (pan-1 mutants) and thiamine (thi-2 and thi-4 mutants);

(4) purine bases such as adenine (ad-2 through ad-4 and ad-8 mutants), hypoxanthine (ad-2 and ad-3 mutants), inosine, and guanine or guanosine (gua-1 or -2 mutants);

(5) pyrimidine bases such as uracil (pyr-1 through pyr-6);

(6) saturated fatty acids (cel mutants) or unsaturated fatty acids such as $C_{16}$ or $C_{18}$ fatty acids having a double bond in the cis conformation at either the 9- or 11-position, fatty acids with a double bond in the trans configuration at the 9-position, and fatty acids with multiple cis double bonds interrupted by methylene bridges (ufa-1 and -2);

(7) physiologically important ions such as potassium (trk);

(8) sugar alcohols such as inositol (acu mutants and inl mutants) and glycerol; and (9) other organic entities such as acetate (ace mutants), α-ketoglutarate, succinate, malate, formate or formaldehyde (for mutants), p-aminobenzoic acid (pab-1, -2 and -3 mutants), and sulfonamide (sfo mutants at 35° C.).

One specific example based on a nutritional requirement is the Arg B+gene coding for the enzyme ornithine transcarbamylase. This enzyme is present in wild type *A. niger*. Mutants lacking this enzyme (Arg B-strains) can be prepared by usual non-specific techniques, such as treatment with ultraviolet radiation, followed by screening based on an inability to grow on minimal medium, coupled with an ability to grow on a medium containing arginine. Fungi containing this genome will grow on minimal medium if they also include an ArgB+nucleus.

Also useful for forcing heterokaryon formation are genes conferring a resistance to any one of a variety of cytotoxic agents. For example, in an alternative embodiment, one of the parents can have a requirement for a nutrient as well as a resistance to a toxic effect induced by a noxious chemical, an antibiotic or virus, or a harsh environmental conditions such as a predetermined temperature range to which the other parent is sensitive.

Specific examples of noxious chemicals that can exert a toxic effect include acriflavine (resistance conferred by acr generally, with the presence of the shg gene being required for resistance by acr-4 and acr-6); 3-amino-1,2,4-triazole (resistance conferred by acr-2, atr-1, cpc, leu-1 or leu-2)); dyes such as malachite green (resistance conferred by acr-3); caffeine (resistance conferred by caf-1); purine analogs (resistance to 8-azaadenine and 2,6-diaminopurine conferred by aza-1; resistance to 8-azaadenine and 8-azaguanine conferred by aza-2; resistance to 8-azaguanine and 6-mercaptopurine conferred by aza-3; resistance to 6-methylpurine conferred by mep(3) and mep(10); cyanide (insensitivity conferred by cni-1 in the first 24 hours of growth); tetrazolium (resistance conferred by cya-6 and cya-7); cycloheximide (resistance conferred by cyh-1, -2 and -3); chromate (resistance conferred by cys-13); 2-deoxy-D-glucose (resistance conferred by dgr⁻); edeine (resistance conferred by edr-1 and -2); ethionine (resistance conferred by eth-1, by nap in the presence of p-fluorophenylalanine, and by oxD if the ethionine is in the D form); fluoro compounds such as 5-fluorodeoxyuridine, 5-fluorouracil, and 5-fluorouridine (resistance to all three conferred by fdu-2; resistance to 5-fluorouracil being conferred by uc-5in an ammonia-free minimal medium; resistance to 5-fluorodeoxyuridine and 5-fluorouridine being conferred by ud-1), and fluorophenylalanine (resistance conferred by fpr-1 through -6 under certain conditions); 8-azaadenine (resistance conferred by mts); methyl methane sulfonate (insensitive or marginally sensitive for upr-1); surface-active agents such as dequalinium chloride, cetyltrimethyl ammonium bromide, and benzalkonium chloride (resistance conferred by sur-1); and metal ions such as vanadate (resistance conferred by van).

Examples of antibiotics typically exerting a toxic effect include benomyl [methyl-1-(butylcarbamolbenzimidazol-2-yl carbamate](resistance conferred by Bml); antimycin A (insensitivity conferred by cni-1 in the first 24 hours of growth); polyene antibiotics such as nystatin (resistance conferred by erg-1 and -3); and oligomycin (resistance conferred by oli).

Also useful are genes conferring resistance to extremes in various environmental conditions such as a high or low temperature, the lack of oxygen (resistance conferred by an), constant light (resistance conferred by lis-1, -2 and -3) or the absence of light, UV radiation, ionizing radiation, and high or low osmotic pressures. In a particularly preferred embodiment, the resistance to a toxic effect is a resistance to an antibiotic such as ampicillin.

Strains generally useful in the invention can be grown on 1×Vogel's Minimal Medium (N medium) in cotton-plugged test tubes, with supplements being added depending on the phenotype of the strain, such as, for example, histidine, arginine and/or inositol. Typical strains may be obtained, for example, from the Fungal Genetics Stock Center ("FGSC") and from D. D. Perkins, Stanford University. Another *N. crassa* strain believed to be useful is M246-89601-2A (obtained from Dr. Mary Case, University of Georgia, Athens). This strain is a derivative of wild-type 74A, which contains a stable qa-2 mutation (M246), an arom-9 mutation (M6-11), and an inos (io601) mutation. The double mutant qa-2, arom-9, lacks both the biosynthetic and catabolic dehydroquinase activities and is unable to grow on minimal medium without a supplement of aromatic amino acids, such as, for example, phenylalanine at a concentration of about 80 µg per ml.

Useful strains of *A. niger* (ATCC 46951) can be prepared by mutagenizing with UV light to form an isolate that requires ornithine or arginine for growth in a defined minimal media. This strain, which lacks ornithine carbamoyl transferase, has been called arg B (350(−)52). Media for growing *A. niger* or *A. nidulans* are described by Cove, *Biochim Biophys Acta* (1966) 113:51–56.

Standard procedures are generally used for the maintenance of strains and the preparation of conidia (Davis and de Serres, *Methods Enzymol* (1971) 17A:79–141). Mycelia are typically grown in liquid cultures for about 14 hours (25° C.), as described in Lambowitz et al. *J Cell Biol* (1979) 82:17–31. Host strains can generally be grown in either Vogel's or Fries minimal medium supplemented with the appropriate nutrient(s), such as, for example, histidine; arginine; phe, tyr, and/or trp (each about 80 µg per ml); p-aminobenzoic acid (about 2 µg per ml); and inositol (about 0.2 mg per ml).

Many fungal strains with the desired characteristics are publicly available. If not readily available, however, one of ordinary skill in the art can use selection techniques well-known in the art for separating out either the desired mutants or the engineered nuclei providing the desired characteristic. Illustrative parental combinations are shown in the table below.

TABLE 2

| First Nucleus | | Second Nucleus | | |
| --- | --- | --- | --- | --- |
| First Character-istic | Second Property | Second Character-istic | First Property | Fusion Conditions |
| his⁻ | arg⁺ | arg⁻ | his⁺ | minimal medium (MM) |
| his⁻ | bm$^r$ | bm$^s$ | his⁺ | MM + bm |
| cyclohex$^s$ | bm$^r$ | bm$^s$ | cyclohex$^r$ | MM + bm + cyclohex |
| caffeine$^s$ | arg⁺ | arg⁻ | caf-1 | MM + caffeine |
| Thi-2 | wt | aro-6 | wt | MM + thiamine + trp + phe |

As seen in the table, a variety of complementary characteristic/property combinations can be chosen to fit various fusion conditions. In general, the nutrient requirement is manifested by a mutant strain, while the ability to resist certain substances may more conveniently be conferred by modification of the nucleus with an expression system for the resistance gene. Alternatively, the nutritional requirement can be effected using recombinant techniques such as homologous recombination with a transforming vector and the resistance can be conferred by mutation under conditions where the toxic conditions are present.

Construction of Expression Vectors for Heterologous Dimer Subunits

The expression systems containing nucleotide sequences encoding a subunit of a heterologous heterodimer are constructed using well known techniques by inserting the coding sequences into host vectors and into operable linkage with control sequences which are capable of effecting their expression in the ultimate filamentous fungus host.

Intermediate hosts are sometimes used to produce intermediate vectors capable of transforming the ultimate fungal cells. The intermediate bacterial transformants can then be grown to obtain the desired quantities of DNA, which can be used to transform a desired filamentous fungus host. Examples of commonly available bacterial vectors that can serve as intermediate vectors include, for example, pBR322, pUC8 and pUC9. Additional useful intermediate vectors include pHY201, pKBY2, pTZ18R, pX182 and pCVN2.9, pN807, pN846.

Alternatively, the sequences encoding the desired subunit can be amplified using standard amplification techniques such as PCR. The coding sequences are then inserted into suitable vectors operably linked to control sequences which affect their expression in filamentous fungi. These vectors can conveniently contain a selectable marker so that successful transformants can easily be identified. The host strain will have characteristics, however, which facilitate its fusion with a complementary host strain as described above.

Thus, to modify the nucleus of the first fungus host strain to contain an expression system for a DNA encoding a particular subunit of the desired heterologous heterodimer, the practice of the invention employs, unless otherwise indicated, molecular biology, microbiology, and recombinant DNA techniques within the skill of the art. Such techniques are explained fully in the literature. See, e.g., Maniatis et al., *Molecular Cloning: A Laboratory Manual* (1982); D. N. Gover et al. *DNA Cloning: A Practical Approach* (1985) Volumes I and II; *Oligonucleotide Synthesis* (M. J. Gait ed. 1984); *Nuclei Acid Hybridization* (Hames et al. eds. 1985); *Transcription and Translation* (Hames et al. eds. 1984); *Animal Cell Culture* (R. I. Freshney ed. 1986); *Immobilized Cells and Enzymes* (IRL Press 1986); B. Perbal, *A Practical Guide to Molecular Cloning* (1984).

In describing the invention, the following terminology will be used in accordance with the definitions set out below:

A "recombinant host" refers to cells that have been, are or will be transformed with DNA sequences prepared by recombinant techniques, and includes the cell originally transformed and cultures and progeny thereof.

A cell has been "transformed" by exogenous DNA when such exogenous DNA has been introduced into the host cell membrane. For prokaryotes such as bacteria the exogenous DNA may be maintained on an episomal element such as a plasmid. Because filamentous fungi do have nuclei (are eukaryotic), most stably transformed fungus host cells contain the exogenous DNA integrated into a chromosome, so that it is inherited by daughter cells through chromosome replication.

A "heterologous" region of a DNA construct is an identifiable segment of DNA within a large DNA molecule that is not found in association with the larger molecule in nature. Thus, when the heterologous region encodes a gene, the gene will usually be flanked by DNA that does not flank the genomic DNA in the genome of the source organism.

The invention involves the production of "heterologous heterodimers" in the filamentous fungi. In this context, "heterologous" means that the heterodimer is not ordinarily produced by the fungus. "Heterodimer" means that the ultimate product is made up of at least two different sub-units. The dimer may be repeated in the ultimate product as is the case with immunoglobulins. Thus, heterodimers include biological materials having two or more distinct sub-units, often designated as "alpha" portions ("α") and "beta" ("β") portions. Examples include prokaryotic or eukaryotic enzymes, blood proteins, hormones, growth factors, toxins and other proteins from pathogens for vaccines, structural proteins, lymphokines, membrane surface proteins, immunoglobulin, enzyme regulators, transcription regulators, and the like.

Preferred heterodimeric proteins include α- and β-transforming growth factors, α'- and β'-antitrypsin, an immunoglobulin, insulin, hemoglobin, an α- and β-kinase, FSH, LH, hCG, and TSH. Particularly preferred heterodimeric proteins include an immunoglobulin, insulin, FSH, LH, hCG and TSH.

A "nucleotide sequence encoding" a protein is that portion of a sequence for which the transcript is translated into a polypeptide when operably linked to appropriate control sequences. The boundaries of the coding sequence are determined by a start codon at the 5' (amino) terminus and a translation stop codon at the 3' (carboxy) terminus. This coding sequence can be derived from, for example, prokaryotic genes, cDNA from eukaryotic mRNA, genomic DNA sequences from eukaryotic DNA (such as mammalian), or may include synthetic DNA. A polyadenylation signal and transcription termination sequence will usually be located 3' to the coding sequence.

A coding sequence is "operably linked to" control sequences when the control sequences effect the expression of the coding sequence in the appropriate host cell.

An "expression system" is a DNA that contains a coding sequence operably linked to the regions of expression control necessary for expression in a host organism.

In one embodiment of the invention, host cells are converted to spheroplasts for transformation. When spheroplasts are used, a preferred method or preparing them is by enzymatic digestion of the cell walls, for example, by using a chitinase/glutamase mixture. The selection of a suitable enzyme for enzymatic digestion is within the skill of the art. Useful enzymes are those capable of digesting complex polysaccharides, and are found among those known as effective in preparing fungal spheroplasts of a wide variety of fungal species. Specific examples of suitable enzymes include Novozym 234 (an impure mixture of enzymes) and β-glucuronidase. Other suitable methods may be used to form spheroplasts. If suitable methods for cell wall penetration by the use of vectors are identified, however, whole cells of the fungal host may be used along with or instead of spheroplasts.

A general procedure for transforming Neurospora is provided below.

General Procedure for Transformation of N. crassa

Strains of Neurospora crassa generally used include those publicly available from the Fungal Genetics Stock Center, but independently prepares strains can also be used. Mutants may be isolated de novo, as illustrated by Stadler et al. *Genetics* (1966) 54:677–685 and Haas et al. *Genetics* (1952) 37:217–26. Useful strains can also be obtained from D. D. Perkins from Stanford University. Strains are typically grown on 1× Vogel's Minimal Medium ("N medium") in cotton-plugged test tubes, with appropriate supplements being added depending on the strain's phenotype.

Spheroplasts are used as subjects for transformation. To form conidial spheroplasts, the fungus is inoculated onto 25 ml of solid N medium, with appropriate supplements in four to five 125-ml Erlenmeyer flasks, which have been plugged with cotton. The cultures are grown at room temperature for 5–7 days.

The conidia are harvested by adding 10 ml of N medium to each flask, replacing the cotton plug, and swirling the flask. The solids are allowed to settle for a few minutes. The conidial mixture is poured to an autoclaved cheesecloth bag hanging in the mouth of an Erlenmeyer flask and secured with one or more rubber bands. The filtrate is recovered, and the concentration of conidia is determined by a hemocytometer count, with chains being counted as one.

A volume of $2\times10^9$ conidia is added to 150 ml of liquid N medium containing 1.5% sucrose and appropriate supplements. The conidia are germinated in the cotton-plugged flask while shaking (150–200 rpm) for 5–6 hours at room temperature until more than 75% have germinated and the germ tubes are 1–4 conidial diameters in length. The cells are harvested by centrifuging at about 1500–2000 rpm for 10 minutes. The cell pellet is rinsed three times with water.

The pellet is then re-suspended in 10 ml of 1.0 M sorbitol, and the spheroplasts are prepared by enzymatic removal of the tough conidial cell wall with an enzyme under isotonic conditions, to prevent the "bursting" of the spheroplasts as they are formed. The protocol is adapted from the method of Vollmer and Yanofsky, *Proc Natl Acad Sci* USA (1986) 83:4869–73.

Specifically, in a sterile 250 ml Erlenmeyer flask, the conidial suspension is generally added to 50 mg of a solid enzyme sold by Novo Laboratories under the trade name Novozym 234. The mixture is shaken (100 rpm) at 30° C. for about an hour (±10 minutes) to digest the cell wall. The spheroplast formation process is monitored by examining a small aliquot of the mixture microscopically under a cover slip. Spheroplasts can be detected because they lyse osmotically when water is applied to one end of the cover slip. The process should be monitored frequently at the later stages of spheroplast formation.

The spheroplast mixture is decanted into a sterile 15-ml conical centrifuge tube, and the spheroplasts are recovered by centrifuging at 500 rpm (10 minutes) in a swinging bucket table top centrifuge. The resulting pellet is rinsed twice with 10 of 1.0M sorbitol and then once with the following STC solution:

91 g sorbitol;

50 mM Tris. Cl;

50 mM $CaCl_2$;

sufficient NaOH to adjust the pH to 8.0; and sufficient water to make a volume of 500 ml.

The final spheroplast pellet is suspended in a mixture of 16.0 ml STC, 200 µDMSO, and 4 ml of the following PTC solution:

200 g polyethylene glycol sold under the trade name "4000" by Sigma;

50 mM Tris. Cl;

50 mM $CaCl_2$;

sufficient NaOH to adjust the pH to 8.0; and sufficient water to make a volume of 50 ml.

The resulting suspension of spheroplasts can either be used directly or stored frozen in 1.0 ml aliquots at −80° C.

In a sterile, 15-ml screw-cap tube, 2.0 μl of 50 mM Spermidine solution, 5.0 μl of the plasmid DNA to be transfected, such as that containing the expression system for a subunit of the desired heterodimer along with a selectable marker such as benomyl resistance (usually at a concentration of about 1.0 mg/ml) and 5.0 μl of a 5 mg/ml heparin solution are mixed by flicking the tube. The spermidine solution is prepared by dissolving 12.73 mg of spermidine in 1.0 ml TE and adjusting the pH to 8.0, and can be stored at −20° C. The heparin solution is prepared by dissolving 50 mg of the sodium salt of heparin in 10 ml of STC and can be stored in frozen aliquots.

The contents of the tube are briefly spun (pulsed) in a tabletop centrifuge and then placed in an ice bath. About 50–100 μl of thawed spheroplasts are added to the tube. The mixture is then incubated on ice about 30 minutes, but incubation periods of about 20 minutes on ice have been successful. About 1 ml of PTC is added and mixed well by flicking the tube. The mixture is incubated further at room temperature for about 20 minutes.

A Regeneration "Top" Agar is prepared by mixing:

20 ml 50×Vogel's Minimal Medium;

825 ml of water;

182 g sorbitol; and 28 g of agar sold under the trade name Bacto-Difco.

The top agar is autoclaved and 100 ml of a 10×FIGS solution (containing 5 g/l fructose, 2 g/l inositol, 2 g/l1 glucose, and 200 sorbose) is added. 15 ml of the top agar is incubated at 50°–55° C. and poured into the tube containing the spheroplasts and plasmid DNA. The contents are quickly mixed by flicking and inverting the tubes and 2–3 times and then uniformly poured onto a layer of plating "bottom" agar.

The "bottom" agar is prepared by mixing any required supplements, in 1×N medium; autoclaving; and adding 10×FIGS and benomyl (if benomyl resistance is used as a marker) to final concentrations of 1×and 0.5 μg/ml respectively. A volume of 25 ml of "bottom" agar is poured into a petri plate and allowed to harden.

After the top agar has been poured over the bottom agar, bubbles are removed by flaming. The plates are kept in an upright position until the top agar has solidified (about 5 minutes). If the top agar tends to harden prematurely, the bottom agar plates can be prewarmed. Once the top agar has solidified, the plates are incubated in an inverted position at 30° C.

For selection of the *N. crassa* transformants, the host is thus cultured on the appropriate medium (having composition only the transformed cells can utilize or containing an antibiotic to which only transformed cells are resistant) and incubated at about 34° C. An indication of a successful transformation can be seen about 24–36 hours after plating. Stable transformants are generally scored after three days of growth. The incubation period to detect transformants will vary depending on the host strain and the phenotypic marker.

Selected transformants can be screened, expression of the desired protein subunit by standard methods, such as an appropriate ELISA, a colony blot immunoassay, restriction enzyme analysis, filter hybridization, nested deletion subcloning, and the like.

In the present invention, the above-described recombinant techniques are used to produce:

(1) a first fungus having a first characteristic that negatively affects growth under specified conditions but is correctable by a property conferred by a second nucleus; the first fungus now transformed to contain an expression system for a nucleotide sequence encoding a first heterodimer subunit; and (2) a second fungus having a second characteristic that negatively affects growth under specified conditions but is correctable by a property conferred by the first nucleus; the second fungus now contains an expression system for a nucleotide sequence encoding the second subunit, which is different from the first unit.

The resulting first and second strains are the parents used to form the heterokaryons of the invention.

Production of the Heterokaryon

Because the first fungus strain and the second fungus strain are chosen to be homozygous with respect to all heterokaryon compatibility alleles (with the exception of the mating allele when the tol gene is present as explained above), when the first and second fungus are cultured together under conditions wherein neither the first fungus nor the second fungus can survive alone the fungi are fused so that the heterokaryotic fungus of the invention is formed. By hyphal fusion, the different haploid nuclei of the first and second fungi come to coexist in a common cytoplasm. While not wishing to be bound by any theory, applicants believe membrane fusion results from the aggregation of intramembranous particles within each cell, making possible cell contacts between protein-free areas. Rearrangement of the lipids in the contact areas then leads to full fusion.

Because each of the two parents contains a nucleus which effects production of different subunit of the heterodimeric protein desired, the resulting heterokaryon is capable of producing the completed heterodimer comprising both subunits.

The invention heterokaryon is stable, with the two nuclei dividing at about the same rate. When heterokaryons having two (or more) nuclei are formed, it is also possible to form some mononucleated hybrid cells if the nuclei enter mitosis at approximately the same time as they fuse. This type of nuclear fusion does yield heterozygous diploid nuclei when it occurs, but it is rare, and the diploid nuclei formed are usually greatly outnumbered by the haploid nuclei.

Culture Conditions for Production of Heterodimers

The fused, heterokaryotic fungus is maintained under conditions wherein neither the first nor second fungus is viable. For example, if each of the fusing fungal strains carry an auxotrophic requirement different from the other, the only cells capable of growing in culture media where both of the nutrients are absent will be complementary heterokaryons which are also capable of expressing the subunits of the heterodimeric protein. For example, one strain may require an amino acid, such as arginine, while the other strain may require a base, such as adenine. Each strain can be independently maintained on media supplemented with the appropriate extra metabolite, but neither strain can survive alone on minimal media. The heterokaryons, however, will survive on minimal media because each nucleus complements the other's requirement.

A typical minimal medium is shown below:

| MINIMAL MEDIUM | | |
| --- | --- | --- |
| Per liter: | Dextrose | 5.0 g |
| | Salt solution (below) | 50.0 ml |
| | Trace elements (below) | 1.0 ml |
| | ± Agar (Difco) | 12.5 g |
| Adjust to pH 6.5; autoclave 15 minutes. | | |

-continued

| SALT SOLUTION | | |
|---|---|---|
| Per liter: | NaNO$_3$ | 120.0 g |
| | KCl | 10.4 g |
| | MgSO$_4$ | 10.4 g |
| | KH$_2$PO$_4$ | 30.4 g |
| TRACE ELEMENT SOLUTION | | |
| Per liter: | (NH$_4$)$_6$Mo$_7$O$_{24}$.4H$_2$O | 1.1 g |
| | H$_3$BO$_3$ | 11.0 g |
| | CoCl$_2$.6H$_2$O | 1.6 g |
| | CuSO$_4$ | 1.6 g |
| | Na$_2$EDTA | 50.0 g |
| | FeSO$_4$.7H$_2$O | 5.0 g |
| | MnCl$_2$.4H$_2$O | 5.0 g |
| | ZnSO$_4$.7H$_2$O | 22.0 g |

Dissolve components sequentially, boil, cool, adjust pH to 6.5 with KOH.

Thus, to maintain the heterokaryotic filamentous fungus in its heterokaryotic state, external forcing is maintained. Growing the heterokaryotic fungal cells on minimal media "forces" the strains to remain together. If mating types are opposite, the presence of the tol gene can be used to maintain stable (A+a) heterokaryons.

The heterologous dimeric protein is produced by culturing the heterokaryon of the invention under conditions favorable to production of the protein. The heterodimer may be recovered from the culture and purified in accordance with standard techniques adapted, of course, as necessary to preserve the structure of the heterodimer.

Preferably, the heterokaryotic filamentous fungus carries an expression vector that allows the host being cultured to secrete the desired heterodimeric protein directly into a minimal growth medium, so that the heterodimeric protein (s) can be purified directly from cell-free medium. Intracellularly produced heterodimer can be isolated from cell lysates. Useful purification methods in accordance with known procedures are within the skill of the art, such as, for example, molecular size exclusion, ion-exchange chromatography, HPLC, and the like.

It will be understood that this description and disclosure of the invention is intended to cover all embodiments that are within the spirit and scope of the invention. For example, it is within the knowledge of the art to insert, delete or substitute amino acids within the amino acid sequence of an open reading frame without substantially affecting the activity of the molecule, and such heterodimeric subunits with such deletions, additions or substitutions are included in the invention.

The following examples are provided by way of illustration, but are not intended to limit the invention in any way. In these examples, all media were autoclaved. Heat-labile supplements and antibiotics were added after the media had cooled. The components of N medium can be found in the review by Davis and DeSerres, *Methods Enzymol.* (1970) 27A:29-143. When ampicillin is added to media, a final concentration of about 50-100 µg/ml is used.

EXAMPLE 1

Insertion of Heterologous DNA into pXpress

A. An insert containing the α subunit of the human LH gene is gel purified for insertion into the vector. The complete amino acid and nucleotide sequence for this subunit are reported by Boothby, M. et al. *J Biol Chem* (1981) 256:5121-5127 and by Fiddes, J. C. et al. *J Mol Appl Genet* (1981) 1:3-18.

A host vector for expression of the heterodimeric subunits, "pXpress" was prepared as described in PCT application WO93/25663 published 23 Dec. 1993, and in U.S. Ser. No. 08/105,448 filed 12 Aug. 1993 incorporated herein by reference. This vector provides a selectable marker on media containing pfpa for transformants that are homokaryotic for this vector, and also contains an Amp$^r$ gene.

Figure 1B:
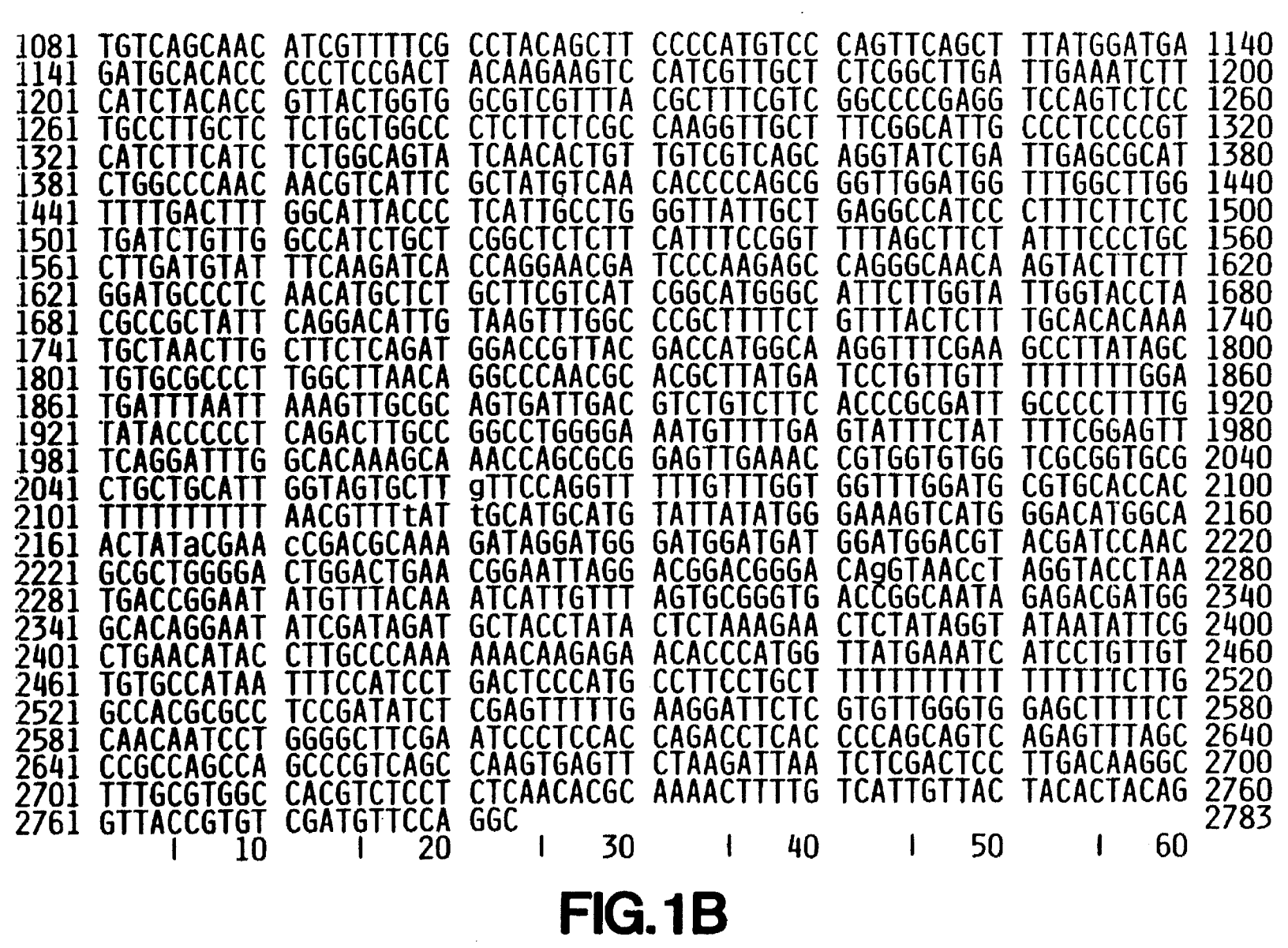

Briefly, the illustrative vector pXpress is constructed from the vector pBN3 which is described in Stuart, W. D., et al., *Genome* (1988) 30:198-203. pBN3 contains the 2783 bp *N. crassa* genomic DNA containing the mtr gene shown in FIG. 1, which is bracketed by a BglII site in the gene and a BamHI site contained in the vector. pBN3 was digested with BamHI and BglII and the segment containing the mtr gene was inserted into the BamHI site of the commercially available vector, pTZ18R, obtained from Pharmacia. This produced clones pN807 and pN816 wherein the EcoRI site contained in the polylinker of the pTZ18R vector is upstream of the ORF; clones in the opposite orientation were designated pN846 and pN839. pXpress is a version of pN846 wherein the 5' polylinker of pTZ18R is deleted. The pXpress vector has useful cloning sites for insertion of the desired DNA in the upstream region just downstream of the mtr promoter (SalI/AccI/HincII) (position 307 in FIG. 1) and also in the latter third of the ORF (HincII at position 1406 and AccI at position 1920).

Five micrograms of pN846 DNA were isolated from *E. coli* NM522 by standard methods (Koo and Stuart *Genome* (1991) 34:644-651). The DNA was double digested with XbaI and HindIII, treated with Klenow and NTPs, cleaned with Geneclean (Bio 101), and ligated with 400 units of DNA T4 polymerase at room temperature overnight. The ligation mixture was used to transform *E. coli* NM522 host cells and selected for Amp$^r$. Transformed colonies were picked and grown in 1.5 ml liquid cultures in tubes overnight. Plasmid DNA was isolated and tested for the presence of HindIII, XbaI and PstI restriction sites. Isolates which had lost the three sites were then tested for the remaining sites expected to be in pN846. One plasmid which had lost the expected sites and retained the expected sites was designated plasmid pXpress.

pXpress is digested with SalI and then with HincII to produce a vector having part of the mtr gene sequence removed, a SalI sticky end overhang at the 5' end at bp 307 following the mtr promoter, and a HincII blunt end site at bp 1406 within the mtr gene ORF.

A sample of 0.5 µg of the αLH subunit ORF provided with suitable restriction sites is ligated into 0.5 µg of pXpress using 40 units of T4 ligase and incubating overnight at 16° C. The fragments ligate, SalI to XhoI, and blunt end HindIII to blunt end HincII (thus losing all four restriction sites).

The ligated fragments are transformed into competent *E. coli* cells DH-5alpha and transformants selected for resistance to ampicillin. Resistant colonies are grown in liquid cultures and a standard preparation is performed to isolate plasmid DNA. The plasmid is digested with the restriction enzyme EcoRV to test the size of the plasmid, i.e., to confirm the presence of the insert. Plasmids testing positive are then digested with BamHI to test the orientation of the insert into the plasmid. Positives are renamed for the desired subunit, pLHα.

B. In a manner exactly analogous to that of paragraph A of this example, the gene encoding LHβ subunit is inserted into pXpress to obtain pLHβ. The complete sequence of this subunit is described by Boorstein, W. R. et al. *Nature* (1982) 300:419-422.

EXAMPLE 2

Transformation of Neurospora Spheroplasts and Expression of LH Subunit

A. Neurospora spheroplasts of strain Y152m14 (which requires histidine) are transformed with pLHα by standard methods. (Koo and Stuart 1991, supra.) The plasmid is linearized by cutting with SacI. A sample of 5 μg of the linearized plasmid is used to transform 1×10⁸ spheroplasts. The mixture is taken up in 15 ml of minimal top agar supplemented with histidine and spread onto a bottom plate containing 0.05 mg/ml p-fluorophenylalanine ("pfpa"). Plates are screened three days later. Colonies are picked and grown on solid Vogel's 1×media containing 0.05 mg/ml pfpa and histidine supplement in tube slants.

Colonies are transferred to liquid cultures of 1×Vogel's with 2% sucrose and histidine in double distilled water. The culture is collected and assayed for the presence of LHα subunit.

B. *N. crassa* strain M246-89601-2A is a double mutant (qa-2, atom-9) that lacks both the biosynthetic and catabolic dehydroquinase activities. This strain is unable to grow on minimal medium without a supplement of at least one aromatic amino acid such as phenylalanine. This strain is transformed with pLHβ using the procedure of paragraph A of this example except that the media are supplemented with phenylalanine rather than histidine. After transfer to liquid culture, as in paragraph A, the cultures are assayed for LHβ subunit.

EXAMPLE 3

Heterokaryon Formation

Both the first and second transformed fungus strains of Example 2 are cultured on a minimal medium lacking histidine and phenylalanine. This medium "forces" the two strains to form heterokaryotic cells having both types of nuclei inside a single septal wall.

The fused, heterokaryotic host is maintained on minimal medium under conditions that favor expression of the α and β subunits. The correctly assembled heterodimeric LH is produced, recovered from the culture and, if desired, purified by conventional techniques.

From the foregoing, it will be appreciated that, although certain embodiments of the invention have been described herein for purposes of illustration, various modifications may be made without deviating from the spirit and scope of the invention. Accordingly, the invention is not to be limited except as by the appended claims.

---

I claim:

1. A heterokaryon filamentous fungus containing a first nucleus and a second nucleus, wherein said first nucleus has been modified to contain an expression system for a first nucleotide sequence encoding a first subunit of a heterologous heterodimer and said second nucleus has been modified to contain an expression system for a second nucleotide sequence encoding a second subunit of said heterologous heterodimer.

2. The fungus of claim 1 wherein the first nucleus confers a first characteristic negatively affecting growth under specified conditions that is corrected by a first property conferred by the second nucleus and the second nucleus confers a second characteristic negatively affecting growth under said specified conditions that is corrected by a second property conferred by the first nucleus under said specified conditions.

3. The fungus of claim 2 wherein the first characteristic is a requirement for a first nutrient; the first property is lack of said requirement; and the specified conditions comprise culture in a medium that lacks said first nutrient.

4. The fungus of claim 3 wherein the second characteristic is a requirement for a second nutrient; the second property is lack of said requirement; and the specified conditions comprise culture in a medium that lacks said first and second nutrients.

5. The fungus of claim 2 wherein the first characteristic is inability to grow in the presence of a first toxic substance; the first property confers resistance to said first toxic substance; and the specified conditions comprise culture in a medium that contains said first toxic substance.

6. The fungus of claim 5 wherein the second characteristic is inability to grow in the presence of a second toxic substance; the second property confers resistance to said second toxic substance; and the specified conditions comprise culture in a medium that contains said first and second toxic substances.

7. The fungus of claim 3 wherein the second characteristic is inability to grow in the presence of a second toxic substance; the second property confers resistance to said second toxic substance; and wherein said specified conditions comprise culture in a medium that lacks said first nutrient and contains said second toxic substance.

8. A method to produce a heterodimer heterologous to a filamentous fungus, which method comprises culturing the fungus of claim 1 under conditions wherein said first and second subunits are produced to form said heterodimer; and recovering the heterodimer from the culture.

9. A method to prepare the heterokaryon fungus of claim 1 which method comprises:

culturing a first fungus containing said first nucleus, wherein said first nucleus confers a first characteristic negatively affecting growth under specified conditions that is corrected by a first property conferred by the second nucleus, along with a second fungus containing said second nucleus wherein said second nucleus confers a second characteristic negatively affecting growth under said specified conditions that is corrected by a second property conferred by the first nucleus;

said culturing being conducted under said specified conditions.

10. The method of claim 9 wherein the first characteristic is a requirement for a first nutrient; the first property is lack of said requirement; and the specified conditions comprise culture in a medium that lacks said nutrient.

11. The method of claim 9 wherein the second characteristic is a requirement for a second nutrient; the second property is lack of said requirement; and the specified conditions comprise culture in a medium that lacks said first and second nutrients.

12. The method of claim 9 wherein the first characteristic is inability to grow in the presence of a first toxic substance; the first property confers resistance to said first toxic substance; and the specified conditions comprise culture in a medium that contains said toxic substance.

13. The method of claim 9 wherein the second characteristic is inability to grow in the presence of a second toxic substance; the second property confers resistance to said second toxic substance; and the specified conditions comprise culture in a medium that contains said first and second toxic substances.

14. The method of claim 9 wherein the second characteristic is inability to grow in the presence of a second toxic substance; the second property confers resistance to said second toxic substance; and wherein said specified conditions comprise culture in a medium that lacks said first nutrient and contains said second toxic substance.

15. The heterokaryotic host of claim 1 wherein said heterodimer is selected from the group consisting of FSH, LH, hCG, TSH, insulin, and an immunoglobulin.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 2783 base pairs
( B ) TYPE: nucleic acid
( C ) STRANDEDNESS: single
( D ) TOPOLOGY: linear ( x i ) SEQUENCE DESCRIPTION: SEQ ID NO:1:

```
AGATCCGCCT CGCCCCAAGC GCATCCCAAC GCGGCGTGCT TATATGTCGC TCTTCCCTCT      60

CACGTACCTC GCAAGTACCT GTCTCATCTG GCACCCGCCT TCTCCATCCC TCTTCTTCAG     120

TACTTAATCT GCCCCGGTCC CCCGCAGTTC ATCCTGTCTC TCAGACCTTG GATCGTCTGT     180

TGGTCTTTTC GCTTATTGTC CGTACCCCCA TCCATATTTA TTCCTGCCTG GGCCCCAGA     240

CAGCATTTTC TCTTTCCCTC CCTCTTTAGC CATCCAAACA GCTTGAGAAG CGAAAATCAA     300

GCCACTGTCG ACAAAGGCCT TCAACAAGGC CTCTTTACCA CCCAACATGG ACTCGCAATA     360

CGAGACAAAA AAGAATGACC CAAACGCCAT CATGCCGTAC CCAGAGTCAA ACGATGAGCA     420

TGTTGGCGAG GTCCGCGGCT TGGGCGGCGG CATCATGGAC AAGGAGCCTG AGGCCCAGGA     480

GGGCCATGCC AAGTTCCACC GTCTCGGCTG GAAACGTCTG ACGGTCGTCC TCATCGTCGA     540

GGCCATTGCC CTCGGCTCTC TCTCGCTTCC CGGCGCCTTC GCTACCCTTG GCATGGTGCC     600

TGGTGTTATT CTCTCTGTCG GCATGGGACT CATCTGCATC TACACGGCTC ACGTTATCGG     660

ACAAACCAAG CTCAAGCACC CTGAAATCGC CCACTATGCC GACGTTGGTC GTGTCATGTT     720

TGGAAGATGG GGATATGAAA TCATCAGCTT CATGTTTGTT CTGCAACTGA TCTTCATCGT     780

CGGCTCCCAC GTCCTCACTG GCACCATCAT GTGGGGCACC ATCACGGATA ACGGCAACGG     840

TACCTGCTCT CTCGTCTTCG GCATTGTCTC CGCCATCATT CTCTTCCTCC TTGCCATTCC     900
```

| | | | | | |
|---|---|---|---|---|---|
|TCCCAGTTTC|GCCGAGGTTG|CCATCCTTGG|ATACATCGAT|TTCGTCTCCA|TCTGCGCCGC|960|
|CATCCTCATC|ACCATGATTG|CTACTGGCAT|TCGCTCGAGC|CACCAGGAGG|GTGGTCTCGC|1020|
|TGCTGTTCCC|TGGTCTTGCT|GGCCCAAGGA|GGACCTTAGC|CTTGCTGAGG|GCTTCATTGC|1080|
|TGTCAGCAAC|ATCGTTTTCG|CCTACAGCTT|CGCCATGTGC|CAGTTCAGCT|TTATGGATGA|1140|
|GATGCACACC|CCCTCCGACT|ACAAGAAGTC|CATCGTTGCT|CTCGGCTTGA|TTGAAATCTT|1200|
|CATCTACACC|GTTACTGGTG|GCGTCGTTTA|CGCTTTCGTC|GGCCCCGAGG|TCCAGTCTCC|1260|
|TGCCTTGCTC|TCTGCTGGCC|CTCTTCTCGC|CAAGGTTGCT|TTCGGCATTG|CCCTCCCCGT|1320|
|CATCTTCATC|TCTGGCAGTA|TCAACACTGT|TGTCGTCAGC|AGGTATCTGA|TTGAGCGCAT|1380|
|CTGGCCCAAC|AACGTCATTC|GCTATGTCAA|CACCCCAGCG|GGTTGGATGG|TTTGGCTTGG|1440|
|TTTTGACTTT|GGCATTACCC|TCATTGCCTG|GGTTATTGCT|GAGGCCATCC|CTTTCTTCTC|1500|
|TGATCTGTTG|GCCATCTGCT|CGGCTCTCTT|CATTTCCGGT|TTTAGCTTCT|ATTTCCCTGC|1560|
|CTTGATGTAT|TTCAAGATCA|CCAGGAACGA|TGCCAAGAGC|CAGGGCAAGA|AGTACTTCTT|1620|
|GGATGCCCTC|AACATGCTCT|GCTTCGTCAT|CGGCATGGGC|ATTCTTGGTA|TTGGTACCTA|1680|
|CGCCGCTATT|CAGGACATTG|TAAGTTTGGC|CCGCTTTCT|GTTACTCTT|TGCACACAAA|1740|
|TGCTAACTTG|CTTCTCAGAT|GGACCGTTAC|GACCATGGCA|AGGTTTCGAA|GCCTTATAGC|1800|
|TGTGCGCCCT|TGGCTTAACA|GGCCCAACGC|ACGCTTATGA|TCCTGTTGTT|TTTTTTGGA|1860|
|TGATTTAATT|AAAGTTGCGC|AGTGATTGAC|GTCTGTCTTC|ACCCGCGATT|GCCCCTTTTG|1920|
|TATACCCCCT|CAGACTTGCC|GGCCTGGGGA|AATGTTTTGA|GTATTTCTAT|TTTCGGAGTT|1980|
|TCAGGATTTG|GCACAAAGCA|AACCAGCGCG|GAGTTGAAAC|CGTGGTGTGG|TCGCGGTGCG|2040|
|CTGCTGCATT|GGTAGTGCTT|GTTCCAGGTT|TTTGTTTGGT|GGTTTGGATG|CGTGCACCAC|2100|
|TTTTTTTTT|AACGTTTAT|TGCATGCATG|TATTATATGG|GAAAGTCATG|GGACATGGCA|2160|
|ACTATACGAA|CCGACGCAAA|GATAGGATGG|GATGGATGAT|GGATGGACGT|ACGATCCAAC|2220|
|GCGCTGGGGA|CTGGACTGAA|CGGAATTAGG|ACGGACGGGA|CAGGTAACCT|AGGTACCTAA|2280|
|TGACCGGAAT|ATGTTTACAA|ATCATTGTTT|AGTGCGGGTG|ACCGGCAATA|GAGACGATGG|2340|
|GCACAGGAAT|ATCGATAGAT|GCTACCTATA|CTCTAAAGAA|CTCTATAGGT|ATAATATTCG|2400|
|CTGAACATAC|CTTGCCCAAA|AAACAAGAGA|ACACCCATGG|TTATGAAATC|ATCCTGTTGT|2460|
|TGTGCCATAA|TTTCCATCCT|GACTCCATG|CCTTCCTGCT|TTTTTTTTT|TTTTTCTTG|2520|
|GCCACGCGCC|TCCGATATCT|CGAGTTTTTG|AAGGATTCTC|GTGTTGGGTG|GAGCTTTCT|2580|
|CAACAATCCT|GGGGCTTCGA|ATCCCTCCAC|CAGACCTCAC|CCCAGCAGTC|AGAGTTTAGC|2640|
|CCGCCAGCCA|GCCCGTCAGC|CAAGTGAGTT|CTAAGATTAA|TCTCGACTCC|TTGACAAGGC|2700|
|TTTGCGTGGC|CACGTCTCCT|CTCAACACGC|AAAACTTTTG|TCATTGTTAC|TACACTACAG|2760|
|GTTACCGTGT|CGATGTTCCA|GGC| | |2783|

( 2 ) INFORMATION FOR SEQ ID NO:2:

( i ) SEQUENCE CHARACTERISTICS:
        ( A ) LENGTH: 1472 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 1..1353

( i x ) FEATURE:
        ( A ) NAME/KEY: CDS ( B ) LOCATION: 1413..1469

( x i ) SEQUENCE DESCRIPTION: SEQ ID NO:2:

| | | | | | | | | | | | | | | | | |
|---|---|---|---|---|---|---|---|---|---|---|---|---|---|---|---|---|
| ATG | GAC | TCG | CAA | TAC | GAG | ACA | AAA | AAG | AAT | GAC | CCA | AAC | GCC | ATC | ATG | 48 |
| Met | Asp | Ser | Gln | Tyr | Glu | Thr | Lys | Lys | Asn | Asp | Pro | Asn | Ala | Ile | Met | |
| 1 | | | | 5 | | | | | 10 | | | | | 15 | | |
| CCG | TAC | CCA | GAG | TCA | AAC | GAT | GAG | CAT | GTT | GGC | GAG | GTC | CGC | GGC | TTG | 96 |
| Pro | Tyr | Pro | Glu | Ser | Asn | Asp | Glu | His | Val | Gly | Glu | Val | Arg | Gly | Leu | |
| | | | 20 | | | | | 25 | | | | | 30 | | | |
| GGC | GGC | GGC | ATC | ATG | GAC | AAG | GAG | CCT | GAG | GCC | CAG | GAG | GGC | CAT | GCC | 144 |
| Gly | Gly | Gly | Ile | Met | Asp | Lys | Glu | Pro | Glu | Ala | Gln | Glu | Gly | His | Ala | |
| | | 35 | | | | | 40 | | | | | 45 | | | | |
| AAG | TTC | CAC | CGT | CTC | GGC | TGG | AAA | CGT | CTG | ACG | GTC | GTC | CTC | ATC | GTC | 192 |
| Lys | Phe | His | Arg | Leu | Gly | Trp | Lys | Arg | Leu | Thr | Val | Val | Leu | Ile | Val | |
| | | 50 | | | | 55 | | | | | 60 | | | | | |
| GAG | GCC | ATT | GCC | CTC | GGC | TCT | CTC | TCG | CTT | CCC | GGC | GCC | TTC | GCT | ACC | 240 |
| Glu | Ala | Ile | Ala | Leu | Gly | Ser | Leu | Ser | Leu | Pro | Gly | Ala | Phe | Ala | Thr | |
| 65 | | | | | 70 | | | | | 75 | | | | | 80 | |
| CTT | GGC | ATG | GTG | CCT | GGT | GTT | ATT | CTC | TCT | GTC | GGC | ATG | GGA | CTC | ATC | 288 |
| Leu | Gly | Met | Val | Pro | Gly | Val | Ile | Leu | Ser | Val | Gly | Met | Gly | Leu | Ile | |
| | | | | 85 | | | | | 90 | | | | | 95 | | |
| TGC | ATC | TAC | ACC | GCT | CAC | GTT | ATC | GGA | CAA | ACC | AAG | CTC | AAG | CAC | CCT | 336 |
| Cys | Ile | Tyr | Thr | Ala | His | Val | Ile | Gly | Gln | Thr | Lys | Leu | Lys | His | Pro | |
| | | | 100 | | | | | 105 | | | | | 110 | | | |
| GAA | ATC | GCC | CAC | TAT | GCC | GAC | CTT | GGT | CGT | GTC | ATG | TTT | GGA | AGA | TGG | 384 |
| Glu | Ile | Ala | His | Tyr | Ala | Asp | Leu | Gly | Arg | Val | Met | Phe | Gly | Arg | Trp | |
| | | 115 | | | | | 120 | | | | | 125 | | | | |
| GGA | TAT | GAA | ATC | ATC | AGC | TTC | ATG | TTT | GTT | CTG | CAA | CTG | ATC | TTC | ATC | 432 |
| Gly | Tyr | Glu | Ile | Ile | Ser | Phe | Met | Phe | Val | Leu | Gln | Leu | Ile | Phe | Ile | |
| | 130 | | | | | 135 | | | | | 140 | | | | | |
| GTC | GGC | TCC | CAC | GTC | CTC | ACT | GGC | ACC | ATC | ATG | TGG | GGC | ACC | ATC | ACG | 480 |
| Val | Gly | Ser | His | Val | Leu | Thr | Gly | Thr | Ile | Met | Trp | Gly | Thr | Ile | Thr | |
| 145 | | | | | 150 | | | | | 155 | | | | | 160 | |
| GAT | AAC | GGC | AAC | GGT | ACC | TGC | TCT | CTC | GTC | TTC | GGC | ATT | GTC | TCC | GCC | 528 |
| Asp | Asn | Gly | Asn | Gly | Thr | Cys | Ser | Leu | Val | Phe | Gly | Ile | Val | Ser | Ala | |
| | | | | 165 | | | | | 170 | | | | | 175 | | |
| ATC | ATT | CTC | TTC | CTC | CTT | GCC | ATT | CCT | CCC | AGT | TTC | GCC | GAG | GTT | GCC | 576 |
| Ile | Ile | Leu | Phe | Leu | Leu | Ala | Ile | Pro | Pro | Ser | Phe | Ala | Glu | Val | Ala | |
| | | | | 180 | | | | | 185 | | | | | 190 | | |
| ATC | CTT | GGA | TAC | ATC | GAT | TTC | GTC | TCC | ATC | TGC | GCC | GCC | ATC | CTC | ATC | 624 |
| Ile | Leu | Gly | Tyr | Ile | Asp | Phe | Val | Ser | Ile | Cys | Ala | Ala | Ile | Leu | Ile | |
| | | 195 | | | | | 200 | | | | | 205 | | | | |
| ACC | ATG | ATT | GCT | ACT | GGC | ATT | CGC | TCG | AGC | CAC | CAG | GAG | GGT | GGT | CTC | 672 |
| Thr | Met | Ile | Ala | Thr | Gly | Ile | Arg | Ser | Ser | His | Gln | Glu | Gly | Gly | Leu | |
| | 210 | | | | | 215 | | | | | 220 | | | | | |
| GCT | GCT | GTT | CCC | TGG | TCT | TGC | TGG | CCC | AAG | GAG | GAC | CTT | AGC | CTT | GCT | 720 |
| Ala | Ala | Val | Pro | Trp | Ser | Cys | Trp | Pro | Lys | Glu | Asp | Leu | Ser | Leu | Ala | |
| 225 | | | | | 230 | | | | | 235 | | | | | 240 | |
| GAG | GGC | TTC | ATT | GCT | GTC | AGC | AAC | ATC | GTT | TTC | GCC | TAC | AGC | TTC | GCC | 768 |
| Glu | Gly | Phe | Ile | Ala | Val | Ser | Asn | Ile | Val | Phe | Ala | Tyr | Ser | Phe | Ala | |
| | | | | 245 | | | | | 250 | | | | | 255 | | |
| ATG | TGC | CAG | TTC | AGC | TTT | ATG | GAT | GAG | ATG | CAC | ACC | CCC | TCC | GAC | TAC | 816 |
| Met | Cys | Gln | Phe | Ser | Phe | Met | Asp | Glu | Met | His | Thr | Pro | Ser | Asp | Tyr | |
| | | | 260 | | | | | 265 | | | | | 270 | | | |
| AAG | AAG | TCC | ATC | GTT | GCT | CTC | GGC | TTG | ATT | GAA | ATC | TTC | ATC | TAC | ACC | 864 |
| Lys | Lys | Ser | Ile | Val | Ala | Leu | Gly | Leu | Ile | Glu | Ile | Phe | Ile | Tyr | Thr | |
| | | 275 | | | | | 280 | | | | | 285 | | | | |
| GTT | ACT | GGT | GGC | GTC | GTT | TAC | GCT | TTC | GTC | GGC | CCC | GAG | GTC | CAG | TCT | 912 |
| Val | Thr | Gly | Gly | Val | Val | Tyr | Ala | Phe | Val | Gly | Pro | Glu | Val | Gln | Ser | |
| | 290 | | | | | 295 | | | | | 300 | | | | | |

-continued

| | | | | | | | | | | | | | | | | |
|---|---|---|---|---|---|---|---|---|---|---|---|---|---|---|---|---|
| CCT | GCC | TTG | CTC | TCT | GCT | GGC | CCT | CTT | CTC | GCC | AAG | GTT | GCT | TTC | GGC | 960 |
| Pro 305 | Ala | Leu | Leu | Ser | Ala 310 | Gly | Pro | Leu | Leu | Ala 315 | Lys | Val | Ala | Phe | Gly 320 | |
| ATT | GCC | CTC | CCC | GTC | ATC | TTC | ATC | TCT | GGC | AGT | ATC | AAC | ACT | GTT | GTC | 1008 |
| Ile | Ala | Leu | Pro | Val 325 | Ile | Phe | Ile | Ser | Gly 330 | Ser | Ile | Asn | Thr | Val 335 | Val | |
| GTC | AGC | AGG | TAT | CTG | ATT | GAG | CGC | ATC | TGG | CCC | AAC | AAC | GTC | ATT | CGC | 1056 |
| Val | Ser | Arg | Tyr 340 | Leu | Ile | Glu | Arg | Ile 345 | Trp | Pro | Asn | Asn | Val 350 | Ile | Arg | |
| TAT | GTC | AAC | ACC | CCA | GCG | GGT | TGG | ATG | GTT | TGG | CTT | GGT | TTT | GAC | TTT | 1104 |
| Tyr | Val | Asn 355 | Thr | Pro | Ala | Gly | Trp 360 | Met | Val | Trp | Leu | Gly 365 | Phe | Asp | Phe | |
| GGC | ATT | ACC | CTC | ATT | GCC | TGG | GTT | ATT | GCT | GAG | GCC | ATC | CCT | TTC | TTC | 1152 |
| Gly | Ile 370 | Thr | Leu | Ile | Ala | Trp 375 | Val | Ile | Ala | Glu | Ala 380 | Ile | Pro | Phe | Phe | |
| TCT | GAT | CTG | TTG | GCC | ATC | TGC | TCG | GCT | CTC | TTC | ATT | TCC | GGT | TTT | AGC | 1200 |
| Ser 385 | Asp | Leu | Leu | Ala | Ile 390 | Cys | Ser | Ala | Leu | Phe 395 | Ile | Ser | Gly | Phe | Ser 400 | |
| TTC | TAT | TTC | CCT | GCC | TTG | ATG | TAT | TTC | AAG | ATC | ACC | AGG | AAC | GAT | GCC | 1248 |
| Phe | Tyr | Phe | Pro | Ala 405 | Leu | Met | Tyr | Phe | Lys 410 | Ile | Thr | Arg | Asn | Asp 415 | Ala | |
| AAG | AGC | CAG | GGC | AAG | AAG | TAC | TTC | TTG | GAT | GCC | CTC | AAC | ATG | CTC | TGC | 1296 |
| Lys | Ser | Gln | Gly 420 | Lys | Lys | Tyr | Phe | Leu | Asp 425 | Ala | Leu | Asn | Met 430 | Leu | Cys | |
| TTC | GTC | ATC | GGC | ATG | GGC | ATT | CTT | GGT | ATT | GGT | ACC | TAC | GCC | GCT | ATT | 1344 |
| Phe | Val | Ile 435 | Gly | Met | Gly | Ile | Leu 440 | Gly | Ile | Gly | Thr | Tyr 445 | Ala | Ala | Ile | |
| CAG | GAC | ATT | GTAAGTTTGG | | CCCGCTTTTC | | TGTTACTCT | | TTGCACACAA | | | | | | | 1393 |
| Gln | Asp | Ile 450 | | | | | | | | | | | | | | |

| | | | | | | | | | | |
|---|---|---|---|---|---|---|---|---|---|---|
| ATGCTAACTT | GCTTCTCAG | ATG | GAC | CGT | TAC | GAC | CAT | GGC | AAG | GTT | TCG | AAG | 1445 |
| | | Met 1 | Asp | Arg | Tyr | Asp 5 | His | Gly | Lys | Val | Ser 10 | Lys | |
| CCT | TAT | AGC | TGT | GCG | CCC | TTG | GCT | TAA | | | | | 1472 |
| Pro | Tyr | Ser | Cys 15 | Ala | Pro | Leu | Ala | | | | | | |

( 2 ) INFORMATION FOR SEQ ID NO:3:

( i ) SEQUENCE CHARACTERISTICS:
        ( A ) LENGTH: 451 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|
| Met 1 | Asp | Ser | Gln | Tyr 5 | Glu | Thr | Lys | Lys | Asn 10 | Asp | Pro | Asn | Ala | Ile Met 15 |
| Pro | Tyr | Pro | Glu 20 | Ser | Asn | Asp | Glu | His 25 | Val | Gly | Glu | Val | Arg 30 | Gly Leu |
| Gly | Gly | Gly 35 | Ile | Met | Asp | Lys | Glu 40 | Pro | Glu | Ala | Gln | Glu 45 | Gly | His Ala |
| Lys | Phe 50 | His | Arg | Leu | Gly | Trp 55 | Lys | Arg | Leu | Thr | Val 60 | Val | Leu | Ile Val |
| Glu 65 | Ala | Ile | Ala | Leu | Gly 70 | Ser | Leu | Ser | Leu | Pro 75 | Gly | Ala | Phe | Ala Thr 80 |
| Leu | Gly | Met | Val | Pro 85 | Gly | Val | Ile | Leu | Ser 90 | Val | Gly | Met | Gly 95 | Leu Ile |
| Cys | Ile | Tyr | Thr 100 | Ala | His | Val | Ile | Gly 105 | Gln | Thr | Lys | Leu | Lys 110 | His Pro |

```
Glu  Ile  Ala  His  Tyr  Ala  Asp  Leu  Gly  Arg  Val  Met  Phe  Gly  Arg  Trp
          115                      120                     125
Gly  Tyr  Glu  Ile  Ile  Ser  Phe  Met  Phe  Val  Leu  Gln  Leu  Ile  Phe  Ile
     130                      135                     140
Val  Gly  Ser  His  Val  Leu  Thr  Gly  Thr  Ile  Met  Trp  Gly  Thr  Ile  Thr
145                      150                     155                          160
Asp  Asn  Gly  Asn  Gly  Thr  Cys  Ser  Leu  Val  Phe  Gly  Ile  Val  Ser  Ala
               165                      170                          175
Ile  Ile  Leu  Phe  Leu  Leu  Ala  Ile  Pro  Pro  Ser  Phe  Ala  Glu  Val  Ala
          180                      185                          190
Ile  Leu  Gly  Tyr  Ile  Asp  Phe  Val  Ser  Ile  Cys  Ala  Ala  Ile  Leu  Ile
          195                      200                          205
Thr  Met  Ile  Ala  Thr  Gly  Ile  Arg  Ser  Ser  His  Gln  Glu  Gly  Gly  Leu
     210                      215                          220
Ala  Ala  Val  Pro  Trp  Ser  Cys  Trp  Pro  Lys  Glu  Asp  Leu  Ser  Leu  Ala
225                      230                     235                          240
Glu  Gly  Phe  Ile  Ala  Val  Ser  Asn  Ile  Val  Phe  Ala  Tyr  Ser  Phe  Ala
               245                      250                          255
Met  Cys  Gln  Phe  Ser  Phe  Met  Asp  Glu  Met  His  Thr  Pro  Ser  Asp  Tyr
               260                      265                     270
Lys  Lys  Ser  Ile  Val  Ala  Leu  Gly  Leu  Ile  Glu  Ile  Phe  Ile  Tyr  Thr
          275                      280                     285
Val  Thr  Gly  Gly  Val  Val  Tyr  Ala  Phe  Val  Gly  Pro  Glu  Val  Gln  Ser
     290                      295                     300
Pro  Ala  Leu  Leu  Ser  Ala  Gly  Pro  Leu  Leu  Ala  Lys  Val  Ala  Phe  Gly
305                      310                     315                          320
Ile  Ala  Leu  Pro  Val  Ile  Phe  Ile  Ser  Gly  Ser  Ile  Asn  Thr  Val  Val
               325                      330                          335
Val  Ser  Arg  Tyr  Leu  Ile  Glu  Arg  Ile  Trp  Pro  Asn  Asn  Val  Ile  Arg
               340                      345                     350
Tyr  Val  Asn  Thr  Pro  Ala  Gly  Trp  Met  Val  Trp  Leu  Gly  Phe  Asp  Phe
          355                      360                     365
Gly  Ile  Thr  Leu  Ile  Ala  Trp  Val  Ile  Ala  Glu  Ala  Ile  Pro  Phe  Phe
     370                      375                     380
Ser  Asp  Leu  Leu  Ala  Ile  Cys  Ser  Ala  Leu  Phe  Ile  Ser  Gly  Phe  Ser
385                      390                     395                          400
Phe  Tyr  Phe  Pro  Ala  Leu  Met  Tyr  Phe  Lys  Ile  Thr  Arg  Asn  Asp  Ala
               405                      410                          415
Lys  Ser  Gln  Gly  Lys  Lys  Tyr  Phe  Leu  Asp  Ala  Leu  Asn  Met  Leu  Cys
               420                      425                     430
Phe  Val  Ile  Gly  Met  Gly  Ile  Leu  Gly  Ile  Gly  Thr  Tyr  Ala  Ala  Ile
          435                      440                     445
Gln  Asp  Ile
450
```

(2) INFORMATION FOR SEQ ID NO:4:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:4:

```
Met  Asp  Arg  Tyr  Asp  His  Gly  Lys  Val  Ser  Lys  Pro  Tyr  Ser  Cys  Ala
```

-continued

| 1 | 5 | 1 0 | 1 5 |
|---|---|-----|-----|
| Pro Leu Ala | | | |